US008145431B2

(12) United States Patent
Kloepfer et al.

(10) Patent No.: US 8,145,431 B2
(45) Date of Patent: Mar. 27, 2012

(54) BODY FLUID TESTING COMPONENT FOR SIMULTANEOUS ANALYTE DETECTION

(75) Inventors: Hans G. Kloepfer, Noblesville, IN (US); Thomas Kloepfer, Noblesville, IN (US); Jason Heim, Indianapolis, IN (US); Reinhard Hafellner, Spielberg (AT)

(73) Assignee: Advanced Medical Products GmbH, Leoben (AT)

(*) Notice: Subject to any disclaimer, the term of this patent is extended or adjusted under 35 U.S.C. 154(b) by 769 days.

(21) Appl. No.: 11/393,439

(22) Filed: Mar. 30, 2006

(65) Prior Publication Data

US 2006/0222567 A1 Oct. 5, 2006

Related U.S. Application Data

(60) Provisional application No. 60/667,240, filed on Apr. 1, 2005.

(51) Int. Cl.
*G01N 33/00* (2006.01)

(52) U.S. Cl. ................ 702/19; 702/22; 702/23; 702/25; 340/573.1; 340/539.12; 340/539.13; 422/400; 422/401; 422/402; 422/408; 422/68.1; 422/82.05; 600/300

(58) Field of Classification Search .................... 702/19, 702/22, 23, 25; 340/573.1, 539.12, 539.13; 422/68.1–80, 82.05; 436/164–172; 600/300
See application file for complete search history.

(56) References Cited

U.S. PATENT DOCUMENTS

| | | | | |
|---|---|---|---|---|
| 4,884,764 | A | 12/1989 | Hill | |
| 4,916,441 | A * | 4/1990 | Gombrich | 345/169 |
| 5,110,724 | A | 5/1992 | Hewett | |
| 5,408,535 | A * | 4/1995 | Howard et al. | 382/128 |
| 5,508,200 | A | 4/1996 | Tiffany et al. | |
| 5,710,028 | A | 1/1998 | Eyal et al. | |
| 6,277,072 | B1 | 8/2001 | Bardy | |

(Continued)

FOREIGN PATENT DOCUMENTS

WO WO 03/077511 9/2003

OTHER PUBLICATIONS

Ascensia Care: Products & Services—Products—Ascensia®) CONTOUR®); www.bayercarediabetes.com/prodserv/products (2 pages), Apr. 4, 2004.

(Continued)

*Primary Examiner* — Jill Warden
*Assistant Examiner* — Shogo Sasaki
(74) *Attorney, Agent, or Firm* — E. Victor Indiano; Indiano Law Group, LLC

(57) ABSTRACT

An analyte testing device is provided for use with a mobile processing device having a camera with a lens, a processor for processing an image captured by the lens. The analyte testing device comprises a casing and a test strip positioner. The test strip positioner positions an analyte containing test strip adjacent to the camera lens to permit the camera to capture an image of the analyte containing test strip. A light source is disposed within the casing. The light source is positioned within the casing to illuminate the analyte containing test strip to facilitate the capture of the image of the test strip. Software is contained within the mobile processing device for performing a quantitative analysis of at least one analyte from the captured image, and providing an output of the results of the quantitative analysis.

22 Claims, 11 Drawing Sheets

U.S. PATENT DOCUMENTS

| | | | | |
|---|---|---|---|---|
| 6,295,506 | B1 * | 9/2001 | Heinonen et al. | 702/104 |
| 6,316,264 | B1 | 11/2001 | Corey et al. | |
| 6,383,453 | B1 | 5/2002 | Banauch et al. | |
| 6,413,213 | B1 * | 7/2002 | Essenpreis et al. | 600/300 |
| 6,494,830 | B1 * | 12/2002 | Wessel | 600/300 |
| 6,511,814 | B1 * | 1/2003 | Carpenter | 435/7.21 |
| 6,535,112 | B1 | 3/2003 | Rochschink | |
| 6,551,841 | B1 | 4/2003 | Wilding et al. | |
| 6,555,060 | B1 | 4/2003 | Mauchan et al. | |
| 6,641,533 | B2 * | 11/2003 | Causey et al. | 600/300 |
| 6,696,240 | B1 | 2/2004 | Kloepfer et al. | |
| 6,699,188 | B2 * | 3/2004 | Wessel | 600/300 |
| 6,840,912 | B2 | 1/2005 | Kloepfer et al. | |
| 7,110,901 | B2 * | 9/2006 | Wada et al. | 702/86 |
| 2002/0009389 | A1 * | 1/2002 | Lappe et al. | 422/58 |
| 2002/0081233 | A1 * | 6/2002 | Lappe et al. | 422/82.05 |
| 2002/0123671 | A1 * | 9/2002 | Haaland | 600/300 |
| 2002/0173704 | A1 | 11/2002 | Schulze et al. | |
| 2003/0009088 | A1 | 1/2003 | Korth et al. | |
| 2003/0032077 | A1 * | 2/2003 | Itoh et al. | 435/14 |
| 2003/0049849 | A1 * | 3/2003 | Mori et al. | 436/46 |
| 2003/0092034 | A1 * | 5/2003 | Cooper et al. | 435/6 |
| 2004/0166023 | A1 * | 8/2004 | Lappe et al. | 422/68.1 |
| 2005/0033196 | A1 * | 2/2005 | Alroy | 600/573 |
| 2005/0074362 | A1 * | 4/2005 | Lappe et al. | 422/68.1 |
| 2005/0203353 | A1 * | 9/2005 | Ma et al. | 600/315 |

OTHER PUBLICATIONS

LifeScan OneTouch Ultra Smart Blood Glucose Monitoring System; www.lifescan.com/products/meters/ultrasmart (2 pages), Dec. 4, 2003.

Diabetes Health Connection—FreeStyle Overview; www.diabeteshealthconnection.com/products (2 pages), Feb. 4, 2006.

Knot It for Life Lifestream Plus Cholesterol Monitor Information; www.knowitforlife.com/monitor.asp (1 page), Feb. 10, 2004.

* cited by examiner

BODY FLUID TESTING COMPONENT FOR SIMULTANEOUS ANALYTE DETECTION

PRIORITY CLAIM

The present application claims priority to and the benefits of Kloepfer, U.S. Provisional Patent Application No. 60/667,240 which was filed on 1 Apr. 2005.

I. TECHNICAL FIELD OF THE INVENTION

The present invention relates to methods and devices for testing analysis fluids, and more particularly to a device capable of simultaneously providing quantitative information about multiple test analytes. In a preferred embodiment, the multi-analyte test device can be coupled to or integrated with an existing processing device, such as a personal computer (PC), or a mobile processing device ("MPD"), such as a tablet PC, a mobile telephone, or a personal digital assistant.

II. BACKGROUND OF THE INVENTION

A. Trends in Healthcare. Traditional healthcare services have been concerned primarily with the treatment of disease. However, it is becoming increasingly recognized by medical professionals that while the treatment of disease will always be an important component of healthcare, the focus of healthcare should shift to the monitoring and maintenance of a person's health prior to and during the onset of a disease. It is believed that healthcare expenses can be reduced, and quality of life can be increased by: (1) monitoring health conditions prior to the onset of a disease, so that the disease can be treated earlier; and (2) convincing people to change their lifestyles in ways that reduce the likelihood of disease occurring.

Several medical conditions exist where the monitoring of levels of particular analytes in a person's blood stream are important. For example, the level of analytes such as cholesterol, glucose, and lactate are important parameters to monitor to gain an understanding of the person's over-all health condition, and to provide vehicles for early intervention, when appropriate, to help treat disease conditions early after their onset.

B. Glucose Monitoring and Diabetes. In the year 2000, 3.2 million people died from diabetes. A key to treating diabetes is maintaining appropriate glucose levels in the patient. Tight glucose control in a form of self-monitoring the blood glucose (SMBG) is considered to be the standard of care for diabetes management and treatment.

C. Atherosclerosis and Cholesterol Levels. Coronary Artery Disease ("CAD") caused by atherosclerosis is the leading cause of death in the Western world, and is predicted to be the leading cause of death in the developing world before 2025. In the U.S., over 50 million people are candidates for drug and/or dietary treatment to modify the profiles of their lipids, such as their "good" and "bad" cholesterol. However, such treatments are enhanced if cholesterol levels are monitored.

D. Sports Medicine and Blood Lactate Levels. A growing interest has developed in recent years in measuring blood lactate levels, since blood lactate serves as a marker of anaerobic glucose metabolism in over-trained muscles. Lactate levels are now routinely monitored by most professional and many serious amateur runners, bicyclists, and swimmers, along with people participating in many fitness and wellness programs.

E. Products Available for Monitoring Glucose Levels. A wide variety of products exist currently, that are useable by the consumer to monitor glucose levels. Currently products are available from Roche Diagnostics (ACCU-CHEK® products); Bayer® (ASCENSIA-brand products); Therasense® (Free-Style® brand products); and Lifescan® (ONE-TOUCH® brand products).

Typically, these products consist of stand-alone meters that are used in connection with a blood test strip. To operate these meters, one employs a lancet device that punctures a tiny hole in a high-blood flow body part, such as a finger tip. A drop of blood is harvested from the hole, and placed onto a test strip. On the test strip, the cellular components (e.g. red and white blood cells) of the blood are separated from the plasma component. The plasma component may be reacted with one or more reagents that are embedded on this strip, to cause the reagents to undergo a chemical reaction, and form a reaction product. With many strips, the reaction product is colored. The color can be correlated to the level of glucose in the sample. The test strip is then "read" by the meter, usually by reflectance photometry.

F. Products Available for Monitoring Cholesterol Levels. Several home devices also exist for measuring blood cholesterol levels. Some of these devices are operated similarly to the blood glucose level testing devices described above. Examples of these include the Cardio Chek® and Cardio Chek® professional devices, and the Life Stream®, Three Minute Cholesterol Monitor.

An alternative test methodology is illustrated with the CholesTrac home cholesterol test. The CholesTrac test is a manual system that does not employ an electronic meter. Rather, the person using CholesTrac device visually compares the "color" of the reacted test analyte with a colorant-containing result chart to determine the cholesterol level.

G. Products Available for Monitoring Lactate Levels. Lactate measuring devices also exist that are similar to the blood glucose and cholesterol meter devices described above. Examples of these include the ACCU-TREND® Lactate and ACCUR-SPORT® portable analyzer, along with the Lactate Probe brand portable lactate analyzer. The devices operate similarly to the glucose and cholesterol meters, as a drop of blood is placed on a reagent containing test strip, which is then inserted into a meter.

H. Blood Testing Devices Invented by the Applicants and Their Colleagues. The Applicants, along with their colleagues have invented several devices that can be used in blood testing. These devices include the capillary test strip to separate particulates shown in Hans G. Kloepfer et al., U.S. Pat. No. 6,696,240 (24 Feb. 2004); the Consolidated Body Fluid Testing Device and Method shown in Hans G. Kloepfer et al., U.S. Patent No. 2003/0109777 (12 Jun. 2003); and Hans G. Kloepfer et al., Method and Apparatus for Analyzing an Analysis Fluid, U.S. Published Patent Application No. 2006/0034728, published 16 Feb. 2006. See also Mary G. Kloepfer, U.S. Pat. No. 4,883,764 (28 Nov. 1989).

The Kloepfer et al., '240 patent relates to a capillary strip that is used to separate particulates from whole blood. The Kloepfer device performs the separation of particulate matter from plasma by employing a gradient of capillary force to move the cell and plasma containing blood sample from a sampling portion wherein the blood is deposited on the strip, to a reagent containing testing site. After the blood has reached the reagent containing test site, the cellular components are removed, with only the reacting plasma remaining.

The Kloepfer et al., '777 publication discloses a device that includes all of the disposable blood testing components required to perform a blood test incorporated into a single, easy-to-manufacture unitary component that can be manufactured inexpensively enough to make single use and disposal economically viable. The Kloepfer consolidated testing device includes a unitary body that carries a disinfectant containing swab, a calibratable and moveable lancet, a blood-flow enhancement device, and a test strip.

The Kloepfer '292 application discloses a meter for use in connection with the consolidated body fluid testing device (test wand) disclosed in the '777 Kloepfer Publication. In addition to disclosing an inventive meter, the Kloepfer '728 Publication also discloses improvements in the test wand that facilitate its use with the meter.

Many of the improvements the Applicants and their colleagues have made to test strips and test wands make them more useful for performing blood tests from very small blood samples. Additionally, a transparent test strip is used with the testing wand to permit the meter to detect blood through transmittance photometry or reflectance photometry, rather than being limited to the reflectance photometric methods used with current meters.

The meter disclosed in the Kloepfer et al., '728 Publication has many features in common with other meters, as it includes the common components of: (1) a receptacle for receiving a test strip; (2) a photometry system, including a light source and receiver for performing a photometric analysis of a reagent-reacted blood samples to quantitatively determine the amount of a particular analyte of interest; (3) a processor within the meter to process the results obtained by the photometric analysis to arrive at a quantitative value for the analyte of interest; and (4) a display for displaying the test results to the user.

In summary, the three above-described Kloepfer references disclose an improved test strip and metering system that is believed by the Applicants to be more convenient to use than known systems, and that is capable of being used with smaller samples than known devices. Nonetheless, room for improvement still exists.

For example, improvements can be made to the meter. Currently, most meters employed for measuring blood analytes are single analyte meters that are useful only for performing the particular test for which they are designed. Current meters could be improved by providing a single meter that is capable of performing a test simultaneously on a variety of analytes. A particularly welcome improvement would be to provide a test strip and metering system that was capable of performing these tests from a single blood sample.

One short coming of current meters is that since the single analyte meters are "stand alone" meters, they require their own processing circuitry and/or software to perform many of their functions. Therefore, an improvement to this current situation would be to provide a meter that is capable of utilizing the processing capability of a device, such as a mobile phone, that most potential users already possess, and that contains the processing capability for performing many of the processing tasks currently performed by the meter, to thereby enable the user to reduce the number of devices that he must carry with him. Additionally, adding the meter components to the mobile device should be less expensive than the cost of manufacturing two separate devices.

Another area for potential improvement is to provide the meters with the ability to communicate results to others, to a health provider, or to the user's own computer for later retrieval and storage.

It is an object of the present invention to provide an improved blood testing system, that incorporates one or several of the improvements discussed above.

III. SUMMARY OF THE INVENTION

In accordance with the present invention, an analyte testing device is disclosed for use with a mobile processing device having a camera with a lens, and a processor for processing an image captured by the camera. The analyte testing device comprises a casing and a test strip positioner. The test strip positioner positions an analyte containing test strip adjacent to the camera lens to permit the camera to capture an image of the analyte containing test strip. A light source is disposed within the casing. A light is positioned within the casing to illuminate the analyte containing test strip to facilitate the capture of the image of the test strip.

Processing software is provided for performing a quantitative analysis of at least one analyte from the captured image, and providing an output of the results of the quantitative analysis.

Preferably, transmission software is also provided for transmitting at least one of the captured images and quantitative analysis to the remote receiver.

In a preferred embodiment of the present invention, the analyte containing test strip includes an analyte receiving portion upon which an analyte resides that has undergone a separation and a reaction with a reagent. The camera captures an image of the analyte receiving portion. The analyte receiving portion can include a first analyte receiving portion containing a first analyte having undergone a first reaction with a first reagent, and a second analyte receiving portion containing a second analyte having undergone a second reaction with a second reagent. The camera is positioned to capture an image of the each of the first and second analyte portions, and the software within the mobile processing device is capable of performing a quantitative analysis on each of the first and second analytes.

Also, the casing is preferably movably coupled to the mobile processing device between a testing position and a non-testing position. In the testing position, the camera lens is aligned with a test strip portion to permit the camera to capture an image of the test strip.

In the non-testing position, the camera lens can capture an image without interference from the casing, but during which time, the casing remains coupled to the mobile processing device. In the most preferred embodiment, the mobile processing device comprises a mobile communications device, such as a cell phone; and the casing is hingedly coupled to the mobile communications device to move between the testing and non-testing position. Additionally, the casing can include a cavity for storing a plurality of test strips therein.

The analyte testing device can either take the form of an external device that includes a plug for being coupled to a data port of the mobile processing device; or alternately, can be an internal device that is encased within the housing of the mobile communication device, and that is "hard wired" to the processor of the PD.

Preferably, the device includes a test strip port for receiving a test strip on which the analyte of interest is contained. A light emitting device is provided for either illuminating the test field on which the analyte is contained, or alternately, for projecting light onto the test field. A miniaturized, digital camera, having a lens and image sensors is provided for either receiving the transmitted light, or alternately photographing the illuminated, analyte-containing test field. The digital camera can either comprise a "still" or motion picture type camera. A motion picture type "video" camera would have the advantage of permitting the user to evaluate the process of the reaction and the kinetics of the test procedure.

In a preferred embodiment, the digital information received by the miniaturized digital camera is then directed to a processor for processing. The processor can comprise a processing unit contained within the analyte testing device. Alternately, the processor of the mobile processing device can be employed to process the information. The mobile processing device's display is then employed to display an output from the processor in a human readable form, so that the user may read the information contained on the display to obtain a measurement of the analyte of interest.

The test strip can be designed to permit the measurement of a plurality of analytes simultaneously. Illustratively, a first reagent can be provided for enabling the user to determine cholesterol level; a second reagent provided for enabling the user to determine blood glucose levels; and a third reagent provided to enable the user to determine blood lactate levels.

The test strip and digital camera can be designed to enable the miniaturized digital camera to receive photometric information about each of the plurality of reagents discreetly, so that the output of the digital camera can provide discreet information to the processor about each of the analytes of interest, thus enabling the processor to provide discreet measurements for each of the three analytes without interference from the presence of the other analytes on the test strip.

One feature of the present invention is that the test strip can be designed to employ a plurality of test strip fields where each test strip field contains a reagent that is capable of reacting with a different analyte of interest to provide a colorimetric reaction product, whose color and intensity can be correlated with the quantity of the analyte in the test fluid. Preferably, these plurality of test fields and test results can be obtained through the application of a single "micro" fluid sample, of about one to two microliters placed on a single test strip.

This feature has the advantage of enabling the user to employ a test strip to test for a variety of analytes.

This multiple test field approach has several advantages. One advantage is that the user can test for a plurality of analytes using a single test strip and a single meter. To Applicants' knowledge, consumer-useable blood testing devices currently in use are single analyte devices, that are capable of testing only for a single analyte. As such, if the user wishes to test for three analytes, he must purchase three separate test strips, and three separate meters.

Another important advantage resides in the ability of the user to test for these plurality of samples by using only a very small blood sample. One draw back to patients who are performing self tests is the need to obtain blood samples. To obtain a blood sample, a user is required to pierce a body part, such as a fingertip with a lancet. The blood that bleeds from the tiny puncture hole is then placed onto a test strip. With the current invention, the user need only make one stick in one tissue site, and only obtain one blood sample, to test for multiple analytes, thus reducing the potential number of times the user must stick himself.

Another feature of a preferred embodiment of the present invention is that the testing device can be designed to be coupled to an existing mobile processing device such as a mobile communications device. This feature has the advantage of reducing the number of devices that a user must purchase and carry around with him.

At the time of the writing of this application, mobile processing devices have become ubiquitous. Mobile processing devices can comprise a wide variety of currently known products such as PDAs, cell phones, MP3 players, lap top computers and the like.

Cell phones are especially ubiquitous. A large plurality of the adult population in developed countries carry cell phones. Although small in size, cell phones contain a large amount of processing capability. Some cell phones, such as the Palm Treo 600 and Treo 300 mobile phones contain a very large amount of processing capability, as the Treo models are personal digital assistants that include mobile telephone capabilities. With the large amount of processing capacity available in a device that is already carried by most people, it seems somewhat wasteful to purchase a separate meter that contains its own processing system.

To reduce this duplication, the device of the present invention employs the processing capability of the cell phone (or other mobile processing device). By making the testing device coupleable to a mobile phone, the user can carry around only a single device (his mobile phone), rather than two or more devices, such as a mobile phone and testing meter. Additionally, by obviating the need for separate processing hardware and software for the meter (as the phone's processing hardware and software can be used), the meter can likely be manufactured less expensively, thus reducing the cost to the end user.

A further advantage provided by the use of a mobile processing device that includes a communication capability is that it permits the user to communicate his test results with others. For example, the user can use the mobile phone to transmit his test results to a healthcare provider who can then monitor the patient's test results, and thereby monitor the patient's health. Additionally, the results can be transmitted from the mobile phone to a user's computer, to enable the user to employ his computer's large memory capability to archive his test results. The transmission can take the form of a text message, or graphic display, and can be forwarded as an e-mail type message.

A further feature of the present invention is that the test device is designed to use reagents that produce calorimetric reactions. This use of calorimetric reagents has several advantages. One advantage is that the colorimetric reagents, when used on a clear test field, permit the use of transmittance photometry to measure the color produced in the reaction product to thereby quantify the amount of the analyte of interest in the test samples.

Another advantage obtained through the use of a colorimetric measurement is that it permits the user to visually see the results, thereby permitting the user to make a visual reliability check on the accuracy of the device.

A further advantage obtained by the colorimetric reaction is that it provides a color-containing image of which a photograph can be taken by a miniaturized digital camera contained within the device. This digital image can be used for archival purposes. Alternately, the digital information contained from the digital "photograph" can be employed as the information that is processed by the processor of the mobile processing device to obtain the quantitative analysis of the analyte of interest.

These and other features and advantages of the present invention will become apparent to those skilled in the art upon a review of the drawings and detailed description of the preferred embodiment of the present invention provided herein that represent the best mode of practicing the invention perceived presently by the Applicants.

III. BRIEF DESCRIPTION OF DRAWINGS

IV. DETAILED DESCRIPTION

Figures 1, 2, 3:
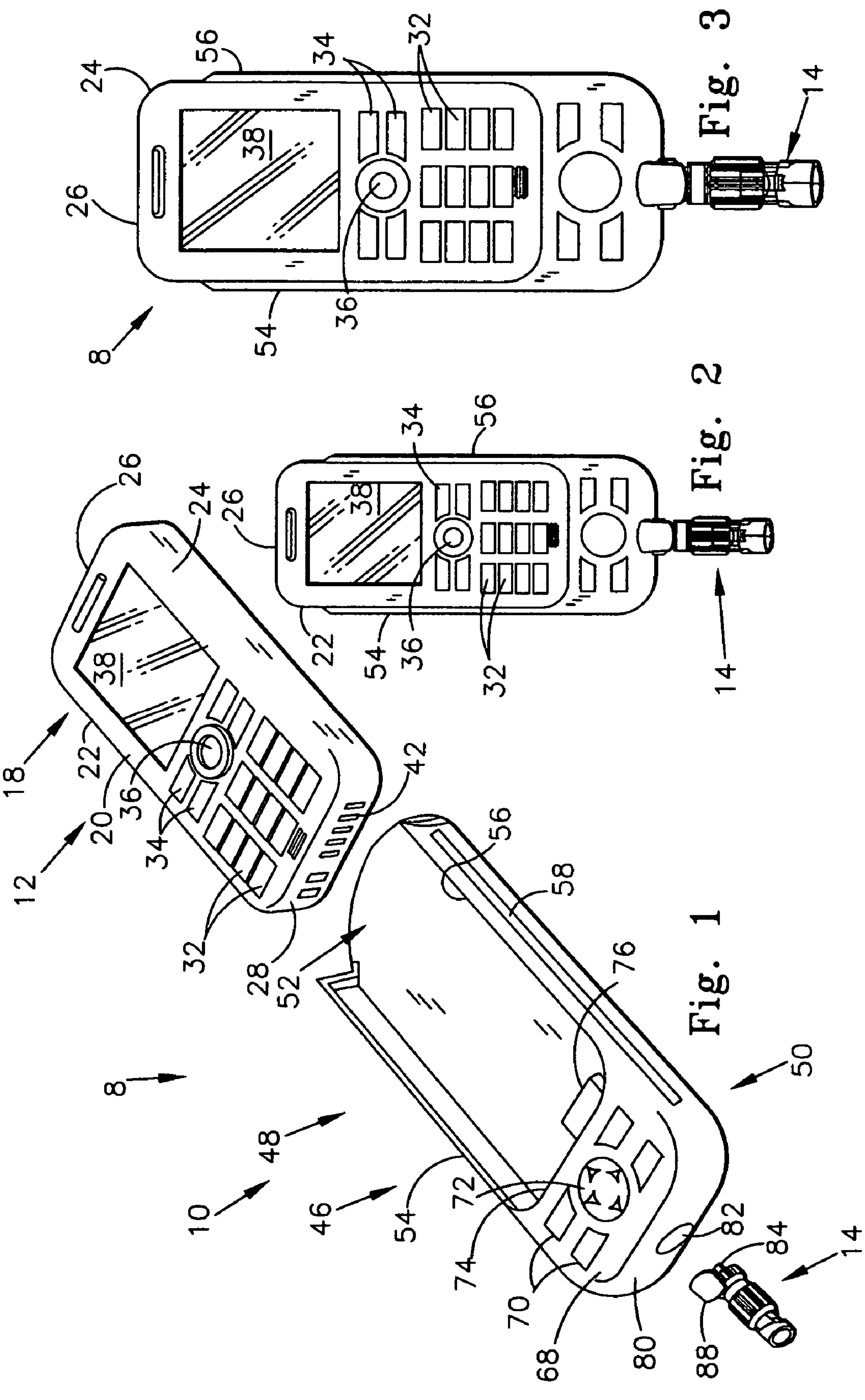
FIG. 1 is a perspective, exploded view of the body fluid testing system of the present invention.
FIG. 2 is a top view of the system.
FIG. 3 is an enlarged, top view of the system.

A body fluid testing system 8 of the present invention is shown in the figures, as being comprised of three primary components. These three components include a body fluid testing analytic unit 10, that is capable of being operatively coupled to mobile processing device, and preferably a mobile communications device, here shown as a mobile telephone 12. The third primary component is a test strip containing test wand 14 that is similar or identical to the ones disclosed in the Kloepfer et al., '777 Publication, and/or the Kloepfer et al., '728 publication, and which includes a test strip similar to the ones disclosed in the Kloepfer '240 patent. The disclosures of these two applications and patent are hereby incorporated by reference into this application.

The most common mobile processing device with which the system 8 will likely be used are mobile communications devices such as mobile phones. The system 8 will likely be used with mobile phones 12 because mobile phone currently have three attributes that contribute to the viability of the present invention. The first attribute is that they generally have fairly robust processors that, through programming (such as by loading software into them), can be made to be capable of processing information received from the analytic unit 10 to create a user-readable output. Some mobile phones currently in use contain a very high level of processing capability, and are currently both capable of being programmed, and performing functions far beyond the typical conversation transmission functions performed by cellular phones. For example, the Palm® Treo® 300, and 600 models comprise personal data assistants, that also include a mobile phone component.

The recently released Palm Treo 700 W has special utility as it is capable of running Microsoft® Windows® mobile applications. Devices such as the Palm Treo 600, 650 and 700 also are equipped with a significant amount of memory, e.g. 64 meg, that can be expanded drastically through the addition of a flash memory card into the already-existing socket provided for receiving same.

Personal data assistants have many of the same functionalities as computers, possessing the ability to run programs, display information, perform calculations and the like. Additionally, other currently existing cell phones have camera capabilities, and thereby the processing capability to process digital picture information, along with the ability to transmit that digital picture information.

The mobile phone 12 includes a housing 18 that encases the electronic components of the mobile phone 12. The housing 18 includes a front surface 20, a first side surface 22, and second side surface 24, a first (top) end surface 26, and a second (bottom) end surface 28. The front surface 20 includes a plurality (usually twelve) of number buttons 32, that the user presses for dialing a phone number, and a plurality of function buttons 34 that the user may push in some predetermined sequence to access and perform the various functions of which the phone 12 is capable of performing. A main function button that can be designed to be a navigator button 36 is disposed between the function buttons 34 of the device shown in the drawing.

An LCD display 30 is also disposed on the front surface 20, and is capable of displaying a significant amount of information. In mobile phone/PDAs, the LCD displays can be quite large (e.g. four square inches), and be capable of displaying a significant amount of information. Optionally, the LCD display 38 may comprise a touch screen that aids the user in navigating through menus and performing the various functions of which the phone 12 is capable. Although not necessary with the present device, a touch-screen type LCD 38 is preferably used, as it facilitates the operation of the device by the user.

A data transfer port 42 is disposed on the bottom end surface 28. A wide variety of data transfer ports exist for use in connection with current PDs. Many of the ports are used not only for transferring data between the device and another device (such as a computer), but are also used to carry voltage and current into the device to recharge the batteries of the mobile phone 12.

The testing device/analytic unit 10 includes a case 46, that includes a cradle portion 48 and a component-containing lower portion 50. The cradle portion 48 is designed to grip and hold the mobile phone 12 to couple the analytic unit 10 to the phone 12. The casing 46 is preferably made from a plastic material and may be constructed as a "clamshell" having two halves connected with a living hinge. The edges of the casing can then be either permanently bonded together through sonic welding (after the components are inserted), or can be held together with a removable fastener such as screws, so that the user may separate the two casing halves, if necessary, to perform servicing of the electronic components contained therein.

The cradle portion 48 includes a rear support member 52 that is placeable adjacent to the rear surface of the housing of the phone 12; a first side support member 54 that is provided for gripping the first side surface 22 of the housing 18 of the phone 12; and a second side support 56 for gripping the second side surface 28 of the housing 18 of the phone 12. Each of the first and second side supports 54, 56 can include a longitudinally extending clip rail 58. As is best shown in FIG. 3, clip rail 58 is provided for enabling a corresponding clip on the test wands 14A-14D to grip the clip rail 58. Through this ability of the test wand 14 to grip on to the clip rail 58, the user can carry around a plurality of test wands 14A-14D on his mobile phones This ability to carry a plurality of test wands 14A-14D is important to persons who are either traveling and must carry several test wands 14 with them, or those who must test their blood multiple times on a daily basis.

The component containing portion 50 of the analytic unit 10 includes an upper surface containing a plurality of operation buttons, including function button 70, and a main or navigator button 72. By pressing one or a combination of the function 70 and navigator 72 buttons, the user can direct the operation of the device. The casing 46 of the analytic unit 10 also includes a phone engaging first end surface 74 that is designed for engaging the bottom end surface 28 of the phone 12. An axially extending plug 76 extends axially outwardly from the phone engaging first end surface 74 and is designed and configured to engage the data port 42 of the phone 12. The casing 46 also includes a wand engaging second end surface 80 that includes a test wand receiving port 82.

Test wand receiving port 82 is sized and configured for receiving and appropriately positioning the test strip 84 (FIG. 4) that is coupled to a test strip holder 86 that is formed as a part of the test wand 14. The test wand receiving port 82 serves as a test strip positioner that is designed to receive a test strip 84 in a proper orientation, to help ensure that the test strip 84 is inserted properly into the meter 12. The test strip 84 is properly oriented into the analytic unit 10 when a major plane of the test strip 84 is generally perpendicular to the plane of the upper surface 68 of the meter 10, so that the camera of the device can capture an image of the analyte containing portion of the test strip 84.

Figure 4:
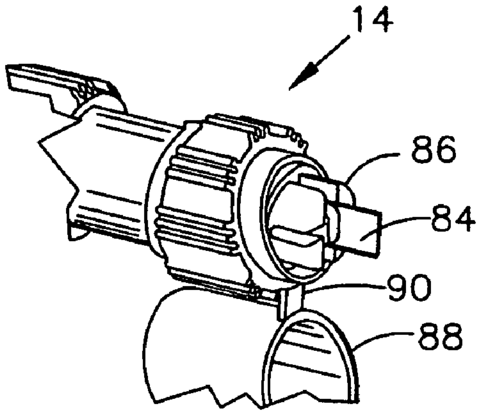
FIG. 4 is an enlarged, perspective view, partly broken away, of a test strip containing test wand useable with the present invention.
Figure 5:
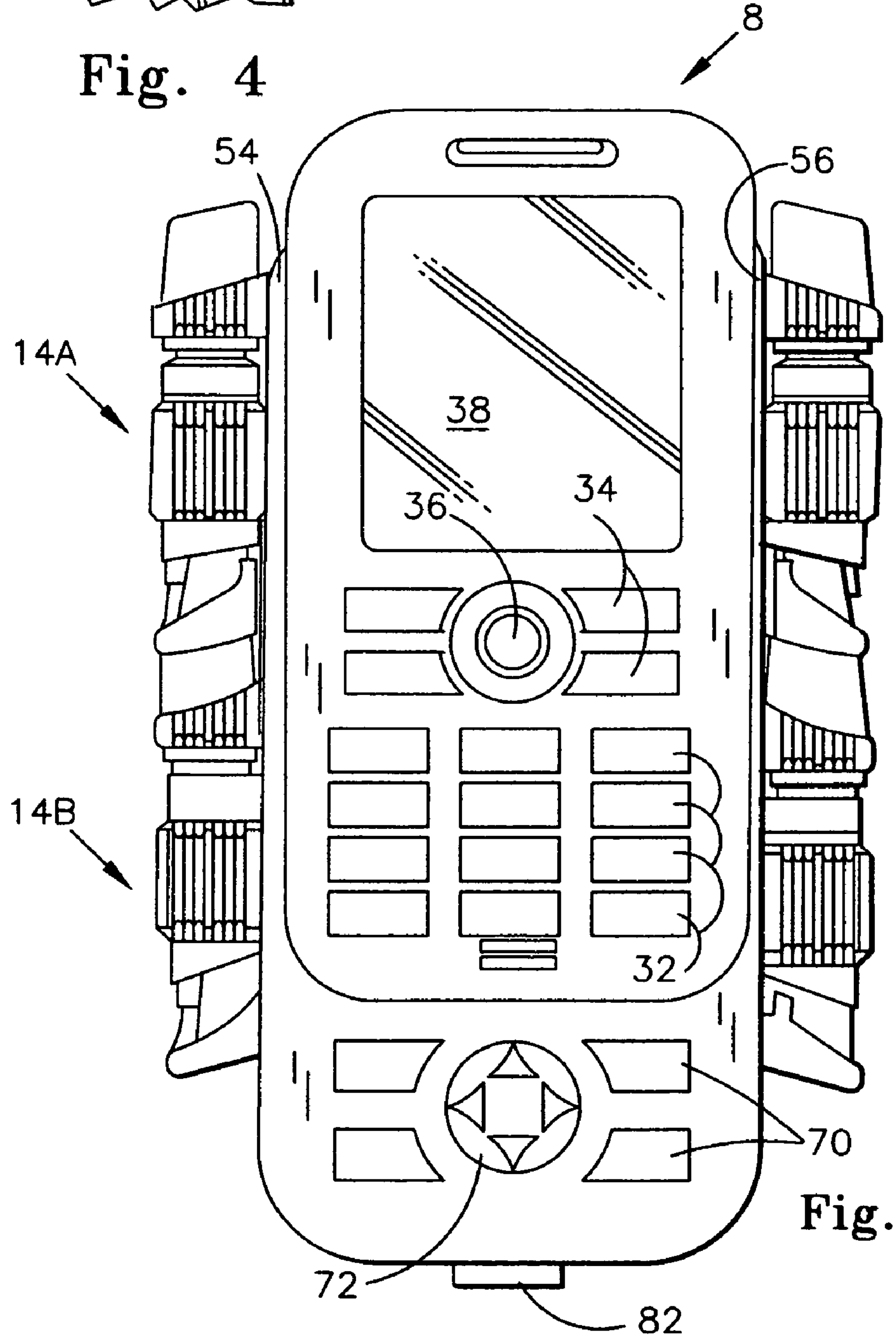
FIG. 5 is a top view of the system of the present invention showing a plurality of test wands coupled thereto.

As best shown in FIG. 4, the test strip 84 is disposed at the end of a test wand 14, and includes an analyte receiving portion for receiving an appropriately separated body fluid that has reacted with an appropriate reagent. However, a hinge 90 hingedly couples a pressure cup 88 to the same end of the test wand 14, so that when not in use, the pressure cup 88 can cover the end of the test strip 84 to prevent contamination or destruction of the test strip 84. The manner in which the pressure cup 88 is used, and the test wand 14 is constructed, is discussed in more detail in the Kloepfer '777 and '728 publications.

As is best shown in FIGS. 8-11, the components of the meter 12 include a printed circuit board 100 that both serves as a base upon which other components are placed, and also as a communication platform to enable electronic communication between the various components. A strip take-up unit 102 is disposed centrally on the printed circuit board 100, and is provided for receiving and properly orienting the test strip 84.

The strip take-up unit 102 includes an axially extending passageway 104, that receives the take-up test strip 84 and a portion of the test strip holder 86. The axially extending passageway 104 is configured to have a vertical slot portion for properly orienting the test strip 84 within the test strip unit 102, so that the test strip 84 will be well positioned for the passage of light therethrough, to perform the test performed by the meter. Preferably, the major plane of the test strip 84 is disposed in a plane perpendicular to the direction of travel of the light path.

A laterally extending passageway 108 is also provided. The laterally extending passageway 108 extends generally perpendicular to the axially extending passageway 104, and intersects the axially extending passageway 104, so that the two passageways 104, 108 are in communication with each other. The primary purpose of the laterally extending passageway 108 is to provide a passageway for the light waves traveling along light path 122, which light waves are emitted by the light source, such as LED 114, and are received by the digital camera 124.

The light source component of the analytic unit 10 includes light source control circuitry 112 that is provided for controlling the operation of the light source 114. As discussed above, the light source 114 preferably comprises an LED-type light. The LED light source 114 emits beams of light that travel through a spread glass or plate 120 disposed in the laterally extending passageway 104 for ensuring a uniform light distribution across the test strip 84.

A miniaturized digital camera 124 is provided for recording a digital image of the reagent reaction products on the test strip 84. The digital camera 124 includes an objective, such as lens 126, and an image sensor for receiving the signals, along with signal processing software for processing signals into a digital picture. The image recorded by the digital camera can be a "picture", or can be signals representative of the light intensity, light wave length ("color"), or other parameter useful for measuring the concentration of the analyte of interest within the reagent reaction product on the analyte receiving portion of the test strip 84.

Similar to most digital cameras, the digital camera 124 of the present invention will likely employ charge-coupled devices (CCDs) for capturing the image of the test strip. A CCD is a sensor for recording images that is in digital photography and astronomy, and consists of an integrated circuit containing an array of linked, or coupled, capacitors. Under the control of an external circuit, each capacitor can transfer its electric charge to one or other of its neighbors.

Digital color cameras generally use a Bayer mask over the CCD. Each square of four pixels has one filtered red, one blue, and two green (the human eye is more sensitive to green than either red or blue). The result of this is that luminance information is collected at every pixel, but the color resolution is lower than the luminance resolution. Better color separation can be reached by three-CCD devices (3CCD) and a dichroic beam splitter prism, that splits the image into red, green and blue components. Each of the three CCDs is arranged to respond to a particular color. Some semi-professional digital video camcorders (and all professionals) use this technique.

The device 8 shown in the figures can operate through a transmissive mode, where the light transmitted by the LED 114 is transmitted in a straight line through the test strip to the video receptor 130 of the digital camera 124. Alternately, the device can be designed to operate in a reflectance type mode, wherein the LED light source, test strips, and video receptor form an angled light path so that the video receptor (lens) captures an image of light emitted from the light source that is reflected off a surface of the test strip.

One of the important attributes of the light 114 and camera 124 used in the analytic unit 10, is that they provide a controlled light environment within the casing wherein a reproduceable and sufficient amount of light is shined upon the test strip 84. By containing the light 114 and camera 124 components within a casing, interference from outside light sources, such as lights within a room, the sun, etc., can be eliminated, thus helping to bolster the reproducibility and accuracy of the tests performed by the device.

Figure 7:
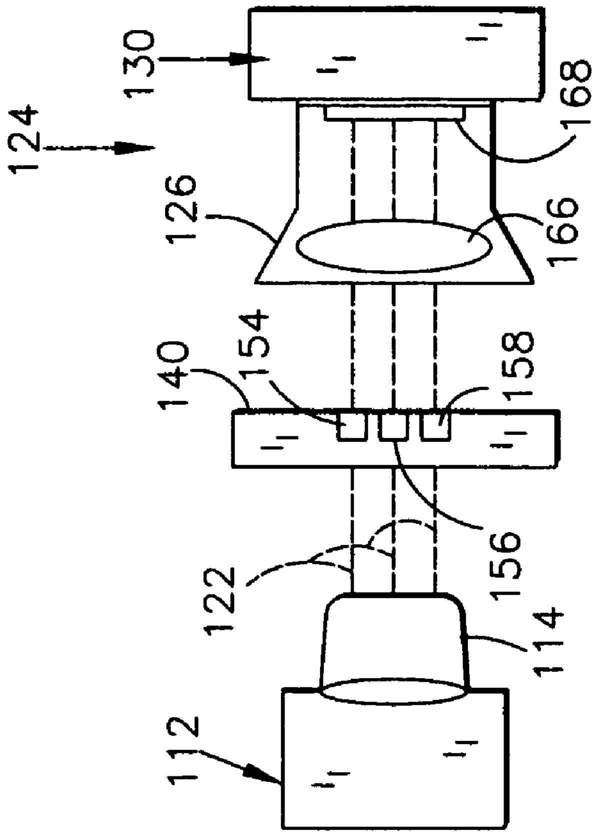
FIG. 7 is a schematic view of the test strip, light source, and digital camera components of the present invention.
Figure 6:
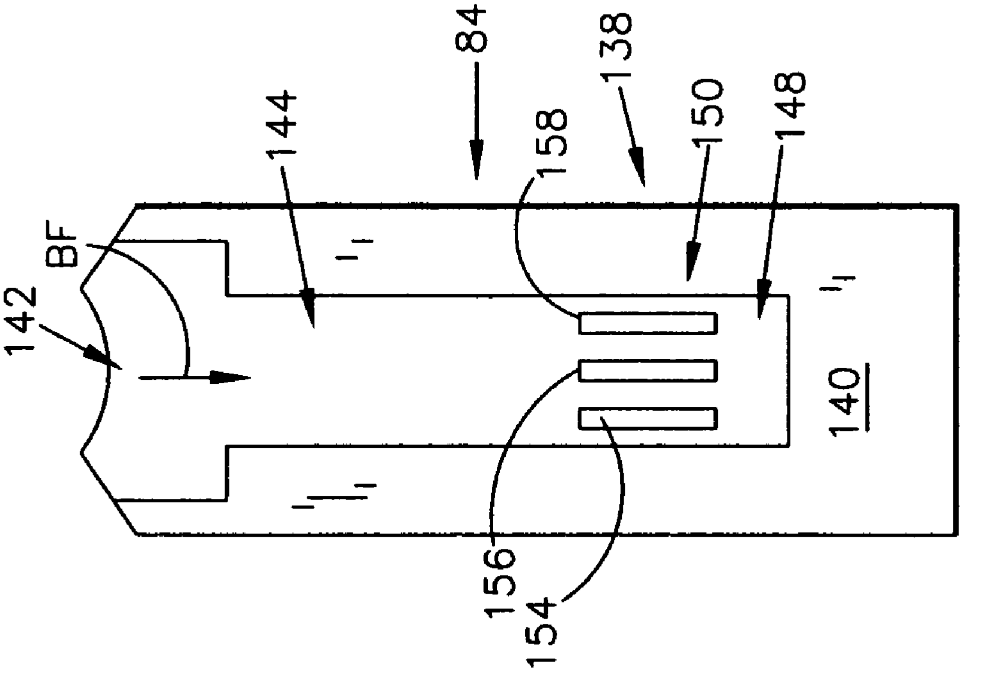
FIG. 6 is a top, greatly enlarged schematic view of a test strip useable with a test wand of the present invention.
Figure 8:
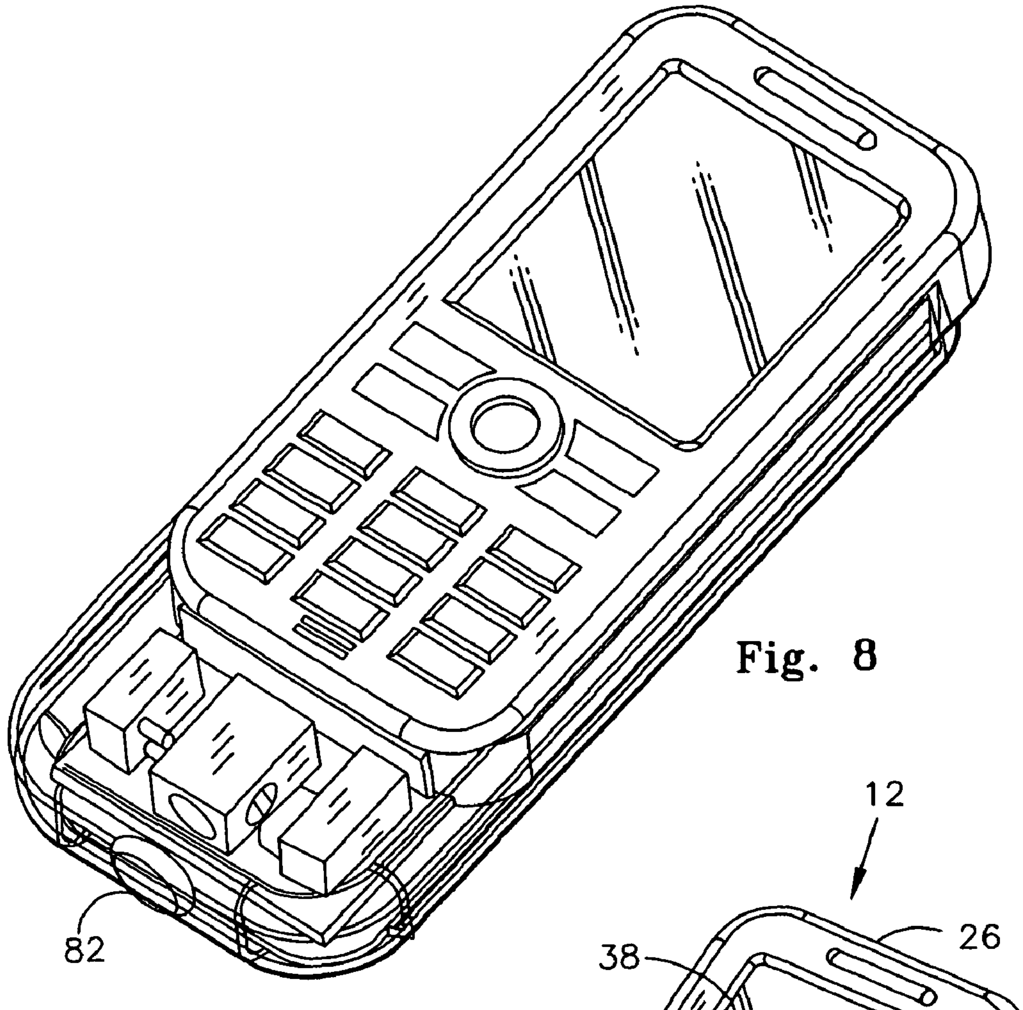
FIG. 8 is a perspective view, with the case of the meter component testing system partly broken away.
Figure 9:
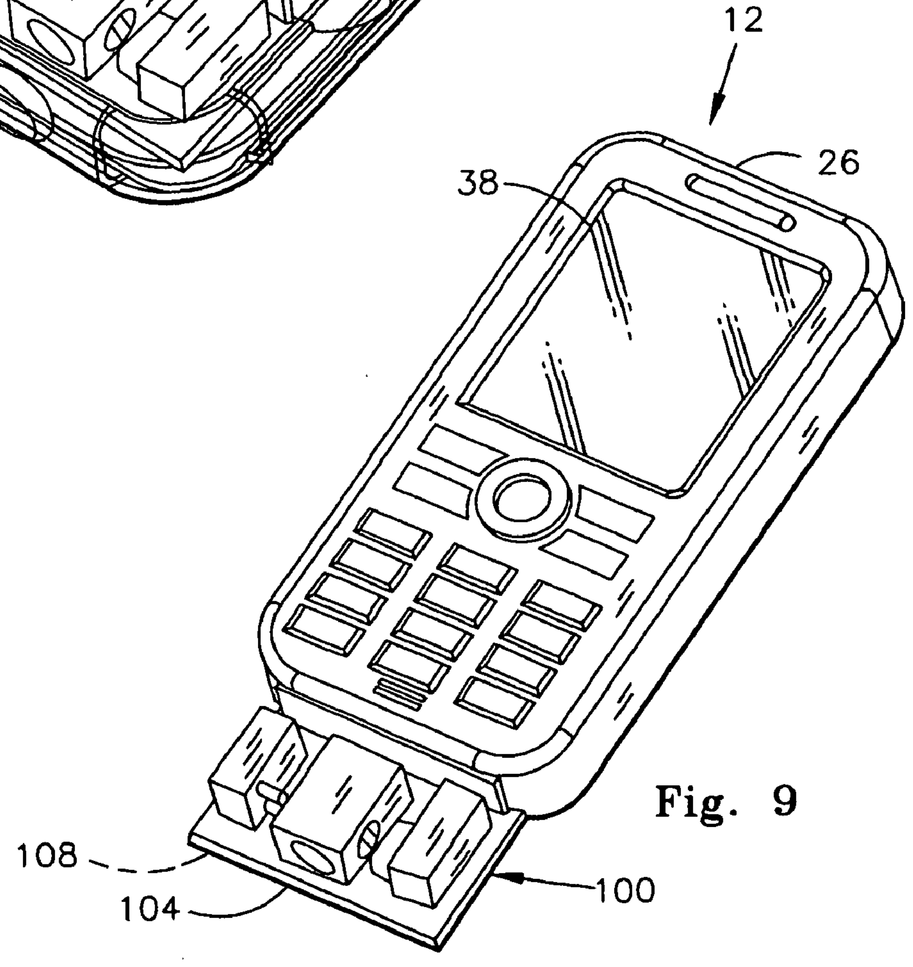
FIG. 9 is a perspective view, with a case of the meter component testing system removed.
Figure 10:
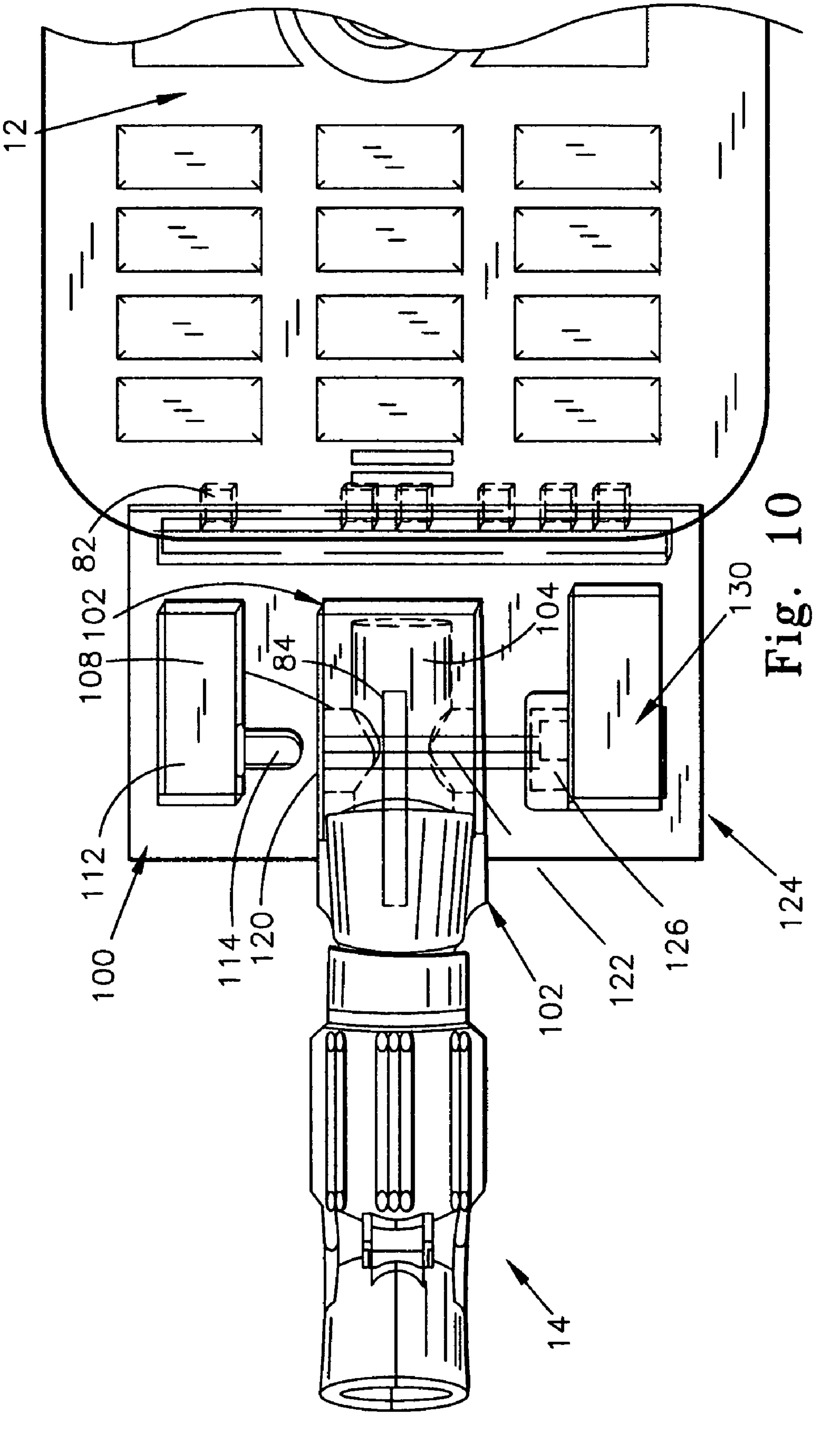
FIG. 10 is an enlarged, somewhat schematic top view, showing a test wand inserted into a strip receiver of the test system of the present invention.
Figure 11:
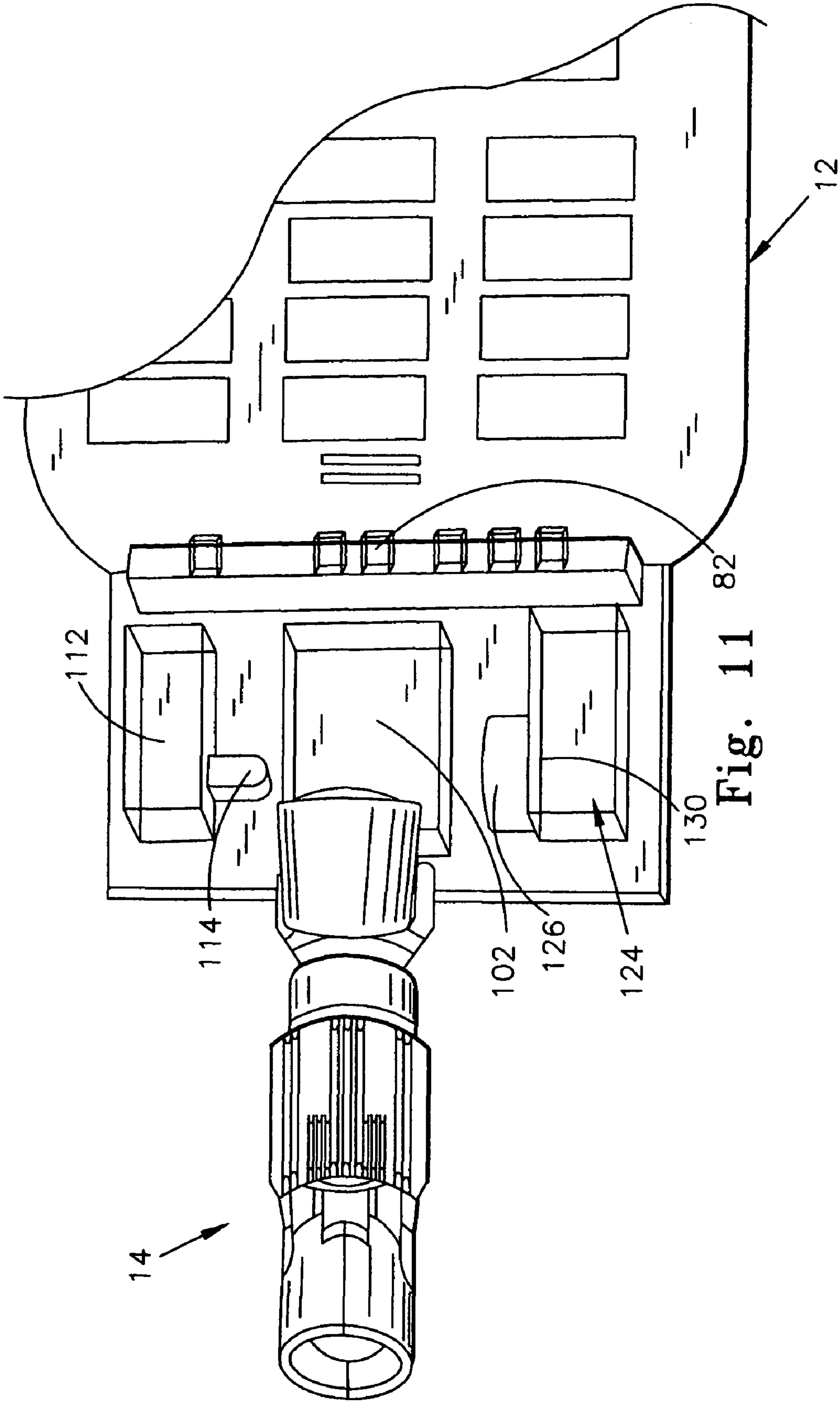
FIG. 11 is another top view, partly broken away of the present invention.

Turning now to FIGS. 6 and 7, the test strip 84 includes a substrate member 138 having an upper surface 140, in which a sample travel path is formed. The sample travel path includes a sample receiving area 142, that is sized and positioned for receiving a drop of body fluid, such as blood, from the patient. As described in more detail in the Kloepfer et al. references described above, a capillary channel 146 is provided for separating the plasma component of the blood from the cellular components such as the red and white blood cells. The cells must normally be separated from the blood in order to obtain an appropriate calorimetric reaction that does not contain interfering colors caused with the colored components of the blood, such as the red and white blood cells.

The capillary channel includes a testing area 150 which comprises an analyte receiving portion 150 upon which reagent strips 154, 156, 158 are placed, and an excess collection area 148 that is disposed downstream of the analyte receiving portion 150 for collecting excess fluids, to ensure that only a proper quantity of fluid remains in the analyte receiving portion 150. As alluded to in this description, a sample of blood is placed in a sample collection area 142, and flows in a direction designated by arrow BF, through the capillary portion 144, where the cellular components are retained. In the testing area, the plasma fluid reacts with the reagents placed on reagent strips 154, 156, 158.

The first 154, second 156 and third 158 reagent strips each may contain a different reagent for testing a different analyte of interest. For example, the first reagent 154 can be a reagent designed to elicit a quantitative colorimetric reaction from a first analyte of interest, such as blood glucose level. Similarly, the second reagent 156 can be a reagent designed to detect the presence of a second analyte of interest, such as blood cholesterol, and the third reagent can be designed for detecting a third analyte of interest such as blood lactate levels.

Alternately, each of the first, second and third reagent strips 154, 156, 158 respectively, can be the same reagent for determining the same analyte of interest. In this case, three reagent strips may be used to provide back ups to each other, or else permit the user to average the values determined by the colorimetric reaction produced by each of the three reagents.

Although the test strip 84 is shown as having a first, second and third 154, 156, 158 reagent strips, it will also be appreciated that more than three or less than three reagent strips can be used, to test a greater or lesser number of analytes of interest. Surprisingly, the Applicants have found that the width of the reagent strip can be reduced to about 1 mm., while still providing a sufficient area so that the digital camera or other sensor will be able to pick up enough appropriate information to provide reliable test strips.

It should also be noted that although the reagents are currently shown as being "reagent strips" 154, 156, 158, the shape and dimension of the reagent placements can vary. For example, the reagents' "strips" can be replaced by a plurality of reagent "dots".

Figure 12:
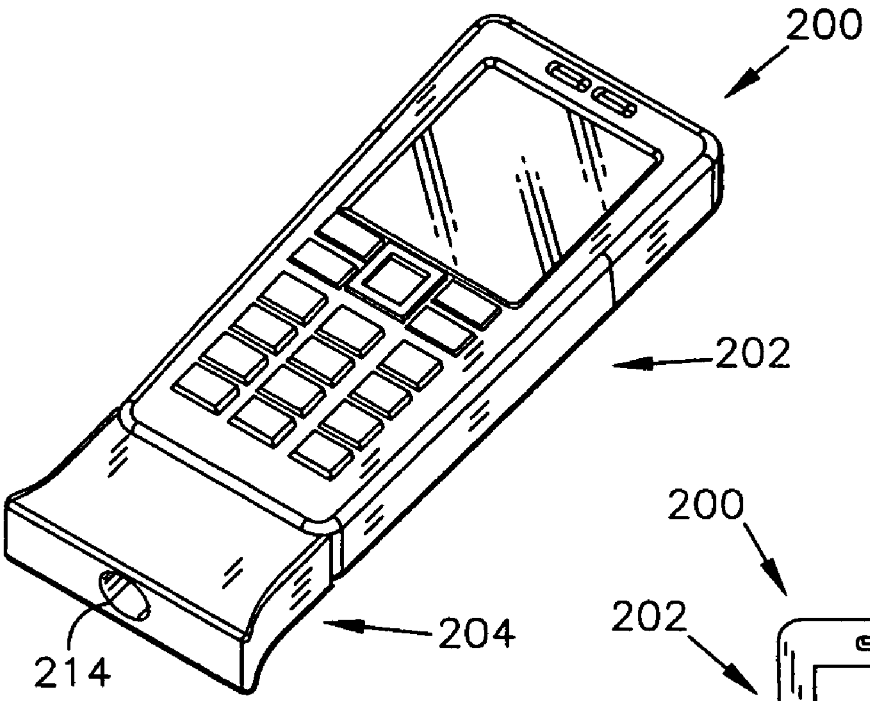
FIG. 12 is a perspective view of an alternate embodiment device.
Figure 13:
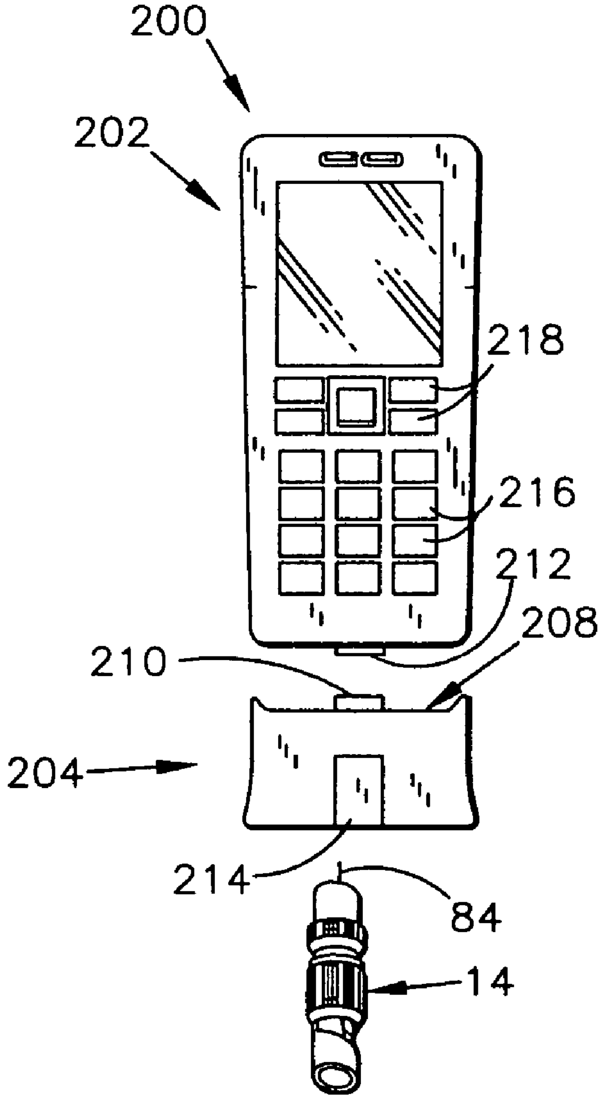
FIG. 13 is a top, exploded view showing an alternate embodiment device useable with an alternate embodiment MPD, and a test wand.

An alternate embodiment blood testing system 200 is shown in FIGS. 12 and 13. Testing system 200 is virtually identical to testing system 10. The main difference between the two is that the blood testing device 204, has a different shaped casing, and different shaped data port plug 210, to better fit the particular model of mobile phone 202 shown in the drawings. It will also be noted that the casing of the testing device 204 does not include the side rail structures or back support structure of the casing shown in FIGS. 1-11.

The blood testing device (analytic unit) 204 includes a top surface 208, that may or may not include a series of function buttons. The function buttons can be eliminated if the device is designed so that the act of connecting the plug 210 to the data receiving port 212 activates the phone 202 to recognize the analytic unit 204, and to display operational information on the LCD screen. In such case, the operation of the analytic unit 204 is controlled by the number button 216 and function buttons 218 of the cell phone. The blood test device 202 also includes a wand receiving port 214 to receive the test strip 84 of test wand 14.

A second alternate embodiment clamshell—type blood testing device 300 is shown in FIG. 14-20. The testing device 300 includes a phone portion 302 and an analytic unit portion 304. The phone portion 302 is hingedly coupled to the casing 305 of the analytic unit portion 304 by a hinge 306.

The phone portion 302 is generally similar to the mobile phones discussed above, as it includes a front surface 307 having an LCD display 310 thereon. The phone 302 also includes a plurality of number buttons 312 and one or more function buttons 314, which serve the same purposes as in the embodiments discussed above. The phone portion 302 also includes a rear surface 316. One element contained on phone portion 302, which is not described with respect to the phones discussed above is a camera lens 320 that is contained on the rear surface 316. The camera lens 316 is of a type similar to those existing currently on camera containing mobile phones. The lens 320 and built-in digital camera contained within the phone 302 are used on currently existing phones to enable the phone owner to use the cell phone user to take photographs of friends, and whatever else she may desire.

One of the unique features of the embodiment of the device 300 shown in FIGS. 14-20, is that the lens 320 and camera contained within the phone 302 are also usable by a body fluid test system for taking a "picture" of the analyte-containing test strip, to measure one or more analytes of interest that have been tested on the test strip.

Figure 19:
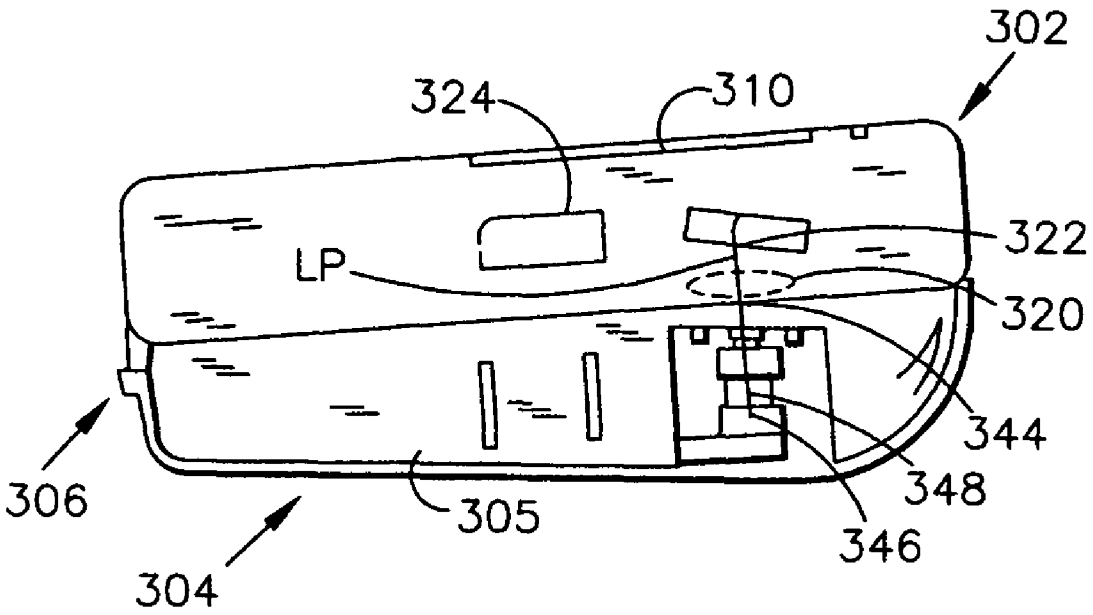
FIG. 19 is a side view, partly in section of the device showing the case in the closed position.

As is best shown in FIG. 19, the lens 320 focuses light onto a photo receptor 322 contained within the interior of the phone portion 302. The photo receptor 322 is coupled to image processing circuitry 324 that is capable of processing the digital image received by the photo receptor 322. As is discussed in more detail in connection with the embodiments described above, the "processing" component of the phone 302 can comprise separate circuitry, or rely on the camera's or phone's already existing circuitry. Additionally, the processor of the phone 302 can include software that is runs on the processor of the phone 302 that can be specifically adapted for performing the analyte test of the present invention.

Figure 14:
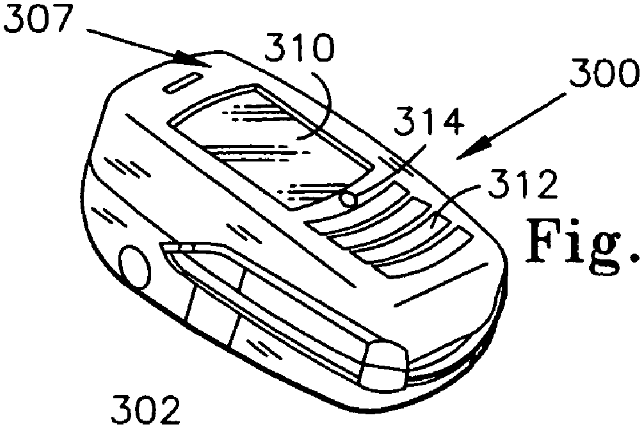
FIG. 14 is a perspective view of a second alternate embodiment of the present invention showing a device with a two-part clamshell like case.
Figure 15:
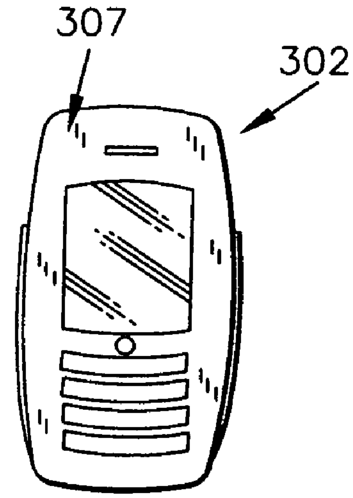
FIG. 15 is a front view of the device.
Figure 16:
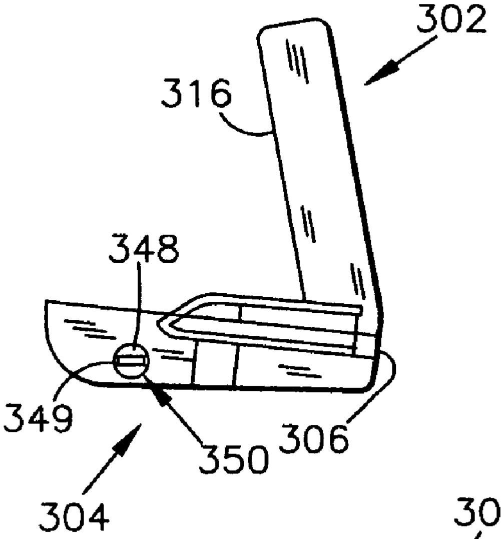
FIG. 16 is a side view of the device showing the case in its open position.
Figure 18:
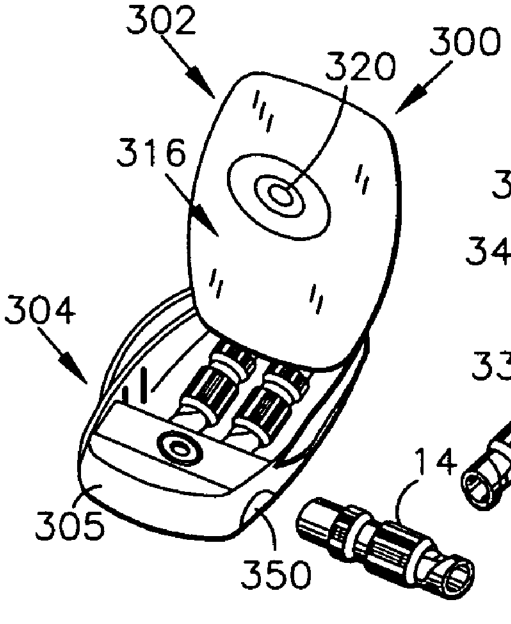
FIG. 18 is another perspective view, showing the case in an open position from a different view point.
Figure 17:
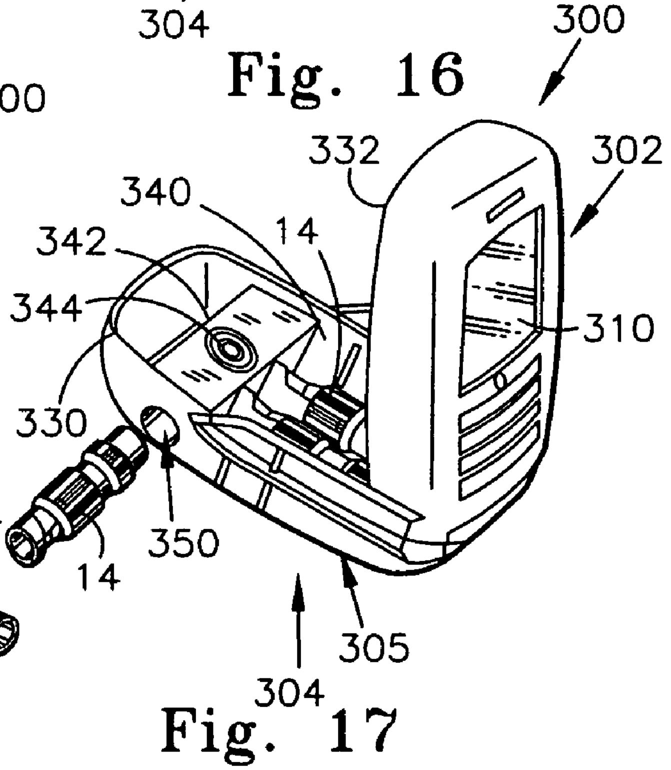
FIG. 17 is a perspective view of the device showing the case in an open position.
Figure 20:
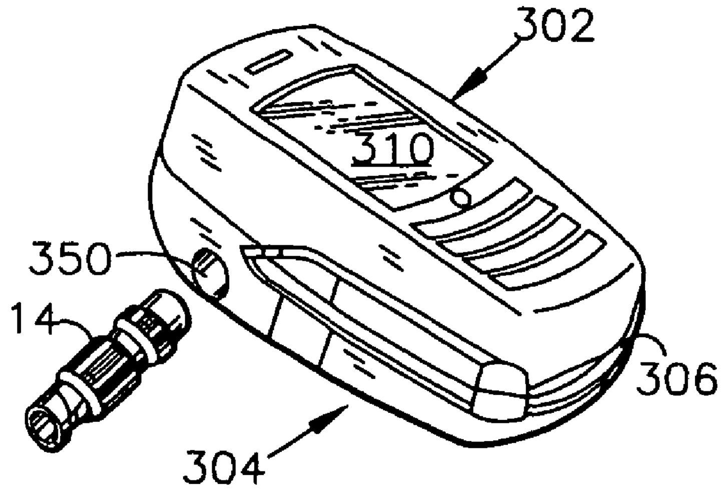
FIG. 20 is an exploded perspective view of the device and a test one of the present invention.

As best shown in FIGS. 17 and 18, the phone portion case 302 includes a lip 332 that is capable of engaging a lip 330 of the analytic unit portion case 304, so that the two portions can be placed a "closed" or "testing" position, as is shown in FIGS. 14, 19, and 20. A latch member (not shown) and release button (not shown) can be employed to respectively latch the two portions 302, 304 together, and release the engagement between the two portions 302, 304. When the release button is actuated to release the latch member, the phone portion 302 and analytic unit portion 304 can be moved about hinge 306 into an "open" or "non-testing" position, similar to that shown in FIGS. 16, 17 and 18. When the casing is in the non-testing or open position, the camera lens 320 becomes unobstructed by the analytic unit portion 304 casing 305, thus enabling the camera to take a picture without interference from the casing. In such a position, for example, a picture of a friend can be taken without the casing becoming a part of the picture.

The analytic unit portion 304 casing 305 includes a generally hollow interior 338, a portion of which defines a wand storage compartment 340. As is shown in FIG. 17, a plurality of wands 14 can be stored in the wand storage compartment 340, to be ready for use when the user so desires.

An objective 342 that includes a light output aperture 344, a light source 346 and a test strip holder 348 is disposed within the hollow interior 338. The light output aperture 344 is positioned to be in an opposed relationship to the lens 320, so that the axis of the light output aperture 344 is colinear with the axis of the lens 320 of the digital camera within the phone 302 when the device 300 is in its closed position.

The device also includes a test strip holder 348 which positions a test strip (e.g. 84) properly in the light path LP when a test wand 14 containing a test strip is inserted into the test wand receiving port 350 that is formed on a side surface of the meter portion case 304. As is best shown in FIG. 19, the light source 346, which may be an LED, shines the light upwardly through a test strip held within the test strip holder 348. This projects the image of the color formed by the analyte reaction products on the strip through the light output aperture 344, through lens 320, and onto the photo receptor 322 of the digital camera contained within the phone 302. This information is then processed by the phone's circuitry and software, into information that ultimately takes the form of information relating to the existence or quantity of the analyte of interest. This information is displayed on the LCD screen 310 of the phone portion 302. The information, along with the image, can also be saved as a file which can then be sent, as an e-mail or "test message" to another device, such as a computer used by a healthcare provider.

Figure 22:
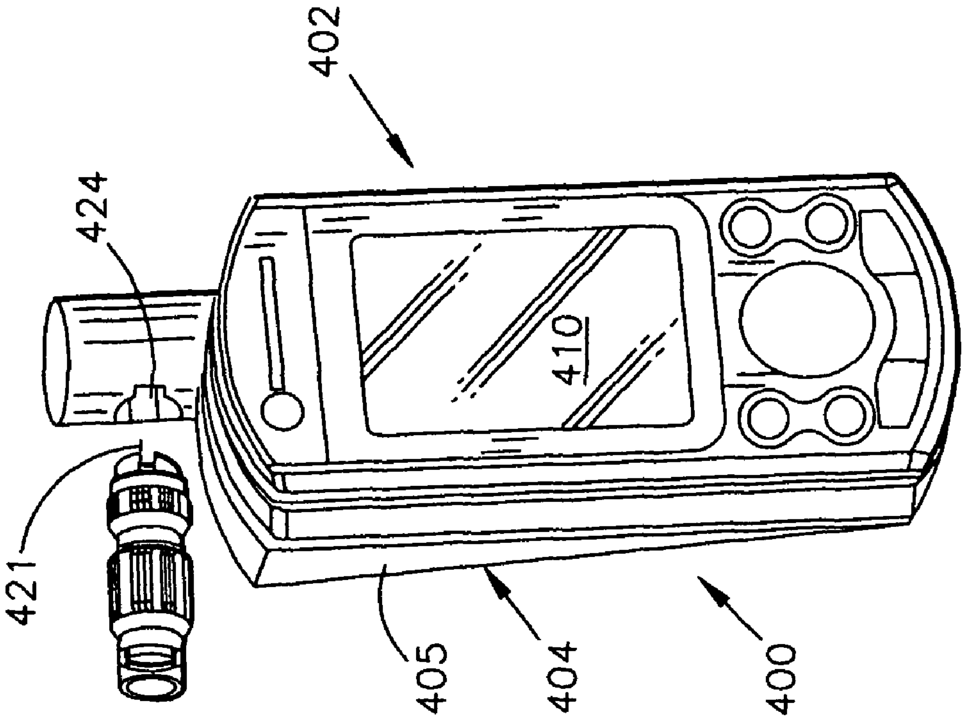
FIG. 22 is a front perspective view of the embodiment of FIG. 21 wherein the camera face is "closed" to hide the number buttons.
Figure 21:
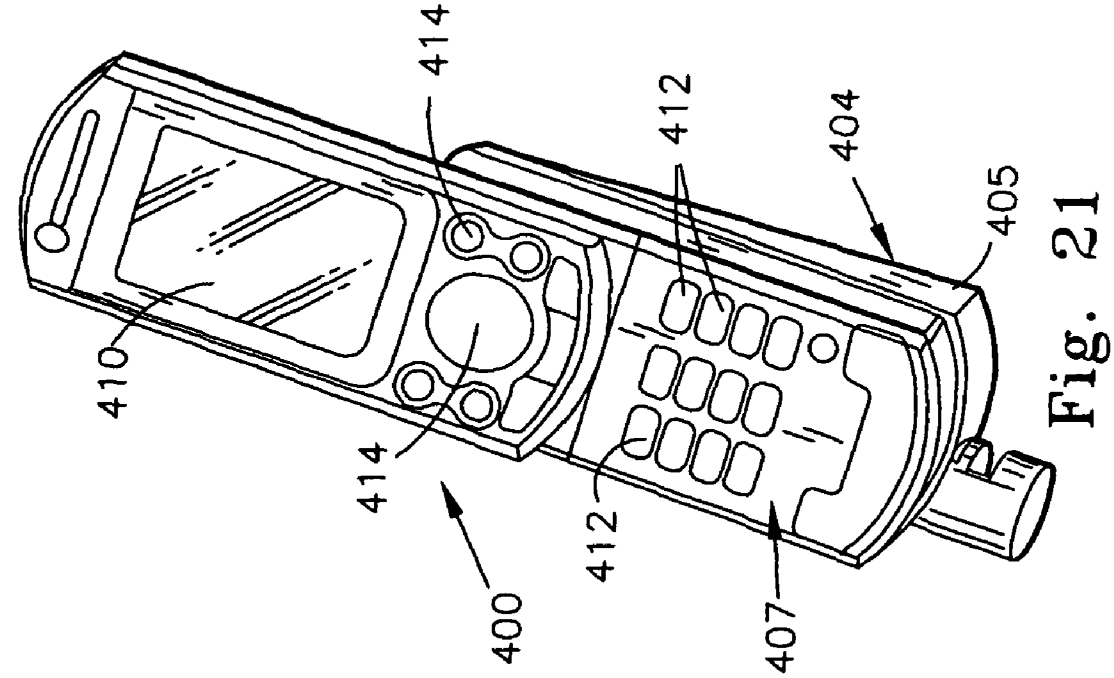
FIG. 21 is a front perspective view of another alternate embodiment of the present invention that employs an optical path diameter that permits an image of a test strip to be captured, even though the test strip positioner positions the test strip out of the normal optical path of the camera lens.
Figure 23:
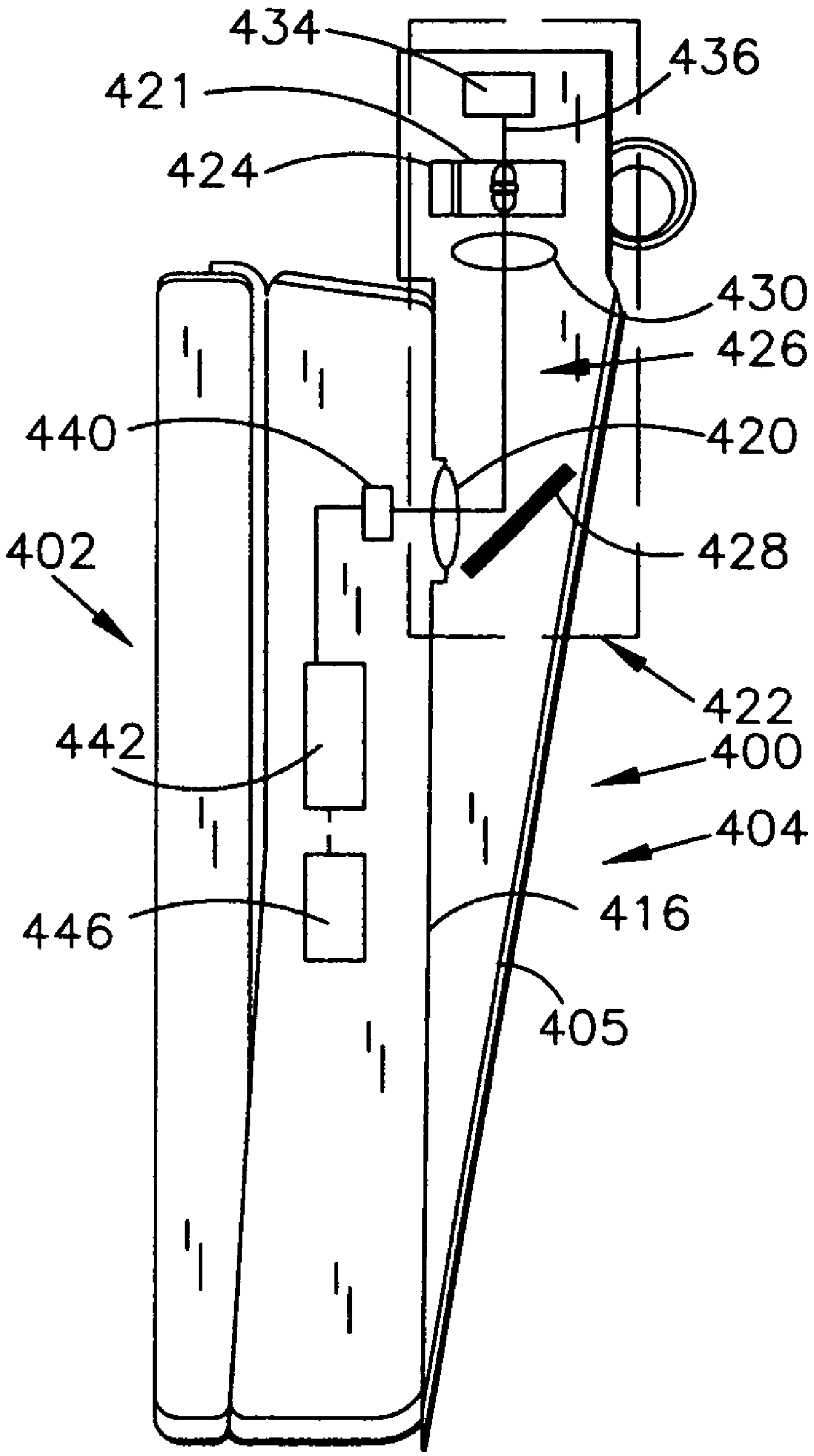
FIG. 23 is a side, schematic view of the alternate embodiment shown in FIG. 21.

A third alternate embodiment analyte testing device 400 is shown in FIGS. 21-23. The testing device 400 includes a phone portion 402 and an analytic unit portion 404. The phone portion 402 is coupled to the casing 405 of the analytic unit portion 404.

The phone portion 402 is generally similar to the mobile phones discussed above, as it includes a front surface 407 having an LCD display 410 thereon. The phone 402 also includes a plurality of number buttons 412 and one or more function buttons 414, which serve the same purposes as in the embodiments discussed above. The phone portion 402 also includes a rear surface 416. Similar to phone portion 302, phone portion 402 includes a camera lens 420 that is contained on the rear surface 416. The camera lens 420 is of a type similar to those existing currently on camera containing mobile phones. The lens 420 and built-in digital camera contained within the phone 402 are used on currently existing phones to enable the phone owner to use the cell phone user to take photographs of friends, and whatever else she may desire.

Similar also to phone 302, the lens 420 and camera contained within the phone 402 are also usable by a body fluid test system for taking a "picture" of the analyte-containing test strip 421, to measure one or more analytes of interest that have been tested on the test strip.

Another difference between device 400 and device 300, is that device 400 includes an optical unit 422, that includes a test positioner 424, that places the test strip 421 in a position that is out of the normal optical path. As will be appreciated, the normal optical path of a lens is the area directly in front of a lens. The optical unit 422 includes an optical path diverter 426 for diverting the light path 436 to test strip 421. The optical path diverter 426 includes a first mirror 428 disposed at a 45° angle to the light path for reflecting light at a 90° angle, from a generally "vertically" directed path (as shown in FIG. 23) to a "horizontally" directed path, that enables the light path to pass through the camera lens 420. Additionally, the optical path diverter 426 includes a first lens, for focusing the light path and the image shown therethrough.

The optical unit 422 of the analytic unit 404 includes a light source 434, such as an LED, that emits the light along a light path 436. The light passes through the test strip 421 that is held in the test strip positioner 424. Light emerging from the test strip 421 (that is passed therethrough) passes through a lens 430, where it is focused. The light path 436 continues to extend to reflecting mirror 428, where the light path is reflected at a 90 degree angle, so that the light can pass through the lens 420 of the camera. Light that passes through the lens 420 is captured by the CCD chip 440 of the digital camera. The image so captured is then conducted to a processor 442.

The processor 442 includes the image processing software, for processing the image. Additionally, the software is capable of processing the image captured by the CCD chip 440, to provide a quantitative analysis of the analyte contained on the analyte receiving portion of the test strip 421. The processor 442 can then transfer the data to the transmitter portion 446 of the cell phone, which itself includes software that permits the image and the quantitative analysis to be transmitted, if desired to a remote source, such as to another computer, another cell phone or to an appropriate storage device.

Having described the above invention in reference to the presently perceived best mode of practicing the invention, it will be appreciated that variations and modifications exist that fall within the spirit of the invention.

What is claimed is:

1. An analyte testing apparatus for providing a quantitative analysis of an analyte of a body fluid placed on an analyte containing test strip, the analyte testing apparatus comprising:

a mobile telephone containing mobile processing device having a digital camera capable of capturing a photographic image of an analyte containing test strip, the digital camera including a lens, the mobile processing device including software operable by the mobile processing device for processing the photographic image captured by the camera to yield an output comprising a quantitative analysis of an analyte on a test strip, and an analyte testing device comprising a casing configured for being coupled to the mobile telephone, the casing including a test strip positioner configured for positioning an analyte containing test strip in a position wherein the camera lens of the mobile telephone is positioned for capturing the photographic image of an analyte containing test strip; and a light source configured and positioned for illuminating an analyte containing test strip to facilitate the capture of the photographic image of an analyte containing test strip taken by the digital camera of the mobile telephone.

2. The analyte testing apparatus of claim 1 further comprising an analyte containing test strip, wherein the analyte containing test strip includes at least one of a first and a second reagent, a first analyte receiving portion containing a first analyte comprising a first body fluid fraction that has undergone a first reaction, and a second analyte receiving portion containing a second analyte comprising a second body fluid fraction that has undergone a second reaction with the second reagent.

3. The analyte testing apparatus of claim 1 further comprising a test strip, and wherein the casing is hingedly coupled to the mobile processing device and is configured for being movable between a testing position wherein the digital camera lens is aligned with the test strip positioner to permit the camera to capture an image of the test strip, and a non-testing position wherein the digital camera lens can capture an image of an object other than that of the test strip without interference from the casing, but wherein the casing remains coupled to the mobile processing device between the testing position and the non-testing position.

4. The analyte testing system of claim 1 wherein the casing comprises an integral casing.

5. An analyte testing apparatus for providing a quantitative analysis of an analyte of a body fluid comprising a mobile telephone containing a mobile processing device including a digital camera having a lens for capturing a digital photographic image on an item in an optical path of the lens, the mobile processing device including software for performing a quantitative analysis on an analyte of a body fluid and providing an output of a result of the quantitative analysis, a test wand including a housing, a test strip for receiving an analyte of a body fluid, and a test strip holder for holding the test strip on to the housing, and a positioner for coupling the test wand to the mobile telephone wherein the analyte of the body fluid on the test strip is positioned in the optical path of the lens of the digital camera so that the digital camera of the mobile telephone is positioned for capturing a digital photographic image of the analyte, so that the image so captured may then be processed by the software for performing a quantitative analysis by the mobile processor to perform the quantitative analysis.

6. The analyte testing apparatus of claim 5 further comprising transmission software loadable into the mobile processing device the transmission software configured for telephonically transmitting both of the captured digital images and the result of the quantitative analysis to a remote receiver.

7. The analyte testing apparatus of claim 5 wherein the casing has an interior, the casing being configured for enclosing the lens of the digital camera and the light source to provide a controlled light environment within the casing interior.

8. The analyte testing apparatus of claim 7 further comprising an analyte containing test strip, wherein the light source, test strip and camera lens are configured to be positioned to define a linear light path wherein the light source shines its light through the test strips and into the camera lens.

9. The analyte testing apparatus of claim 7 further comprising an analyte containing test strip wherein the light source, test strip and camera lens are configured to be positioned to define an angled light path wherein the lens captures an image of light emitted from the light source that is reflected off of a surface of the test strip.

10. The analyte testing apparatus of claim 5 further comprising a first reagent and wherein the analyte receiving portion includes a first analyte receiving portion containing a first analyte comprising a first body fluid fraction that has undergone a first reaction, and a second analyte receiving portion containing a second analyte comprising a second body fluid fraction that has undergone a second reaction with a second reagent.

11. The analyte testing apparatus system of claim 10 further comprising a third reagent, wherein the analyte receiving portion further includes a third analyte receiving portion and a third analyte resident on the third analyte receiving portion, the third analyte comprising a third body fluid fraction that has undergone a third reaction with the third reagent.

12. The analyte testing apparatus of claim 11 wherein the first analyte comprises a body fluid and the reagent comprises a reagent useful for determining blood glucose levels, the second analyte comprises a body fluid and second reagent, the second, reagent being useful for determining blood cholesterol levels, and the third analyte comprises a body fluid and third reagent, the third reagent being useful for determining blood lactate levels.

13. The analyte testing apparatus of claim 5 further comprising a casing that includes a cavity configured for storing a plurality of test strips therein.

14. The analyte testing apparatus of claim 5 further comprising a casing configured to be coupled to the mobile processing device wherein at least one of the lens and casing are movable into a position wherein the lens of the camera is positioned for capturing images of objects other than of the test strip without interference from the casing.

15. The analyte testing apparatus of claim 14 wherein the casing is configured to be movable between a testing position wherein the camera lens is aligned with the positioner to permit the camera to capture an image of the analyte on the test strip; and a non-testing position wherein the lens of the camera is positioned to capture an image of objects other than that of the test strip without interference from the casing, but between the two positions the casing remains coupled to the mobile processing device and wherein the casing includes a cavity for storing a plurality of test strips therein.

16. The analyte testing apparatus of claim 5 further comprising a casing that includes a cavity configured for storing a plurality of test strips therein, and wherein the test strip includes a reagent, an analyte receiving portion, and an analyte resident upon the analyte receiving portion, the analyte including a body fluid that has undergone a separation and a reaction with the reagent, wherein the reagent comprises a first reagent and a second reagent, wherein the analyte receiving portion includes a first analyte receiving portion containing a first body fluid fraction that has undergone a separation and a reaction with the first reagent, and a second analyte receiving portion containing a second body fluid fraction that has undergone a separation and a reaction with the second reagent, wherein the digital camera is configured to captures an image of the first and second analyte receiving portions; and wherein the software contained within the mobile telephone containing mobile processing device is configured for performing a quantitative analysis of each of the first and second separated and reacted body fluid fractions.

17. The analyte testing system of claim 16 wherein the reagent comprises a first reagent and a second reagent, wherein the analyte receiving portion includes a first analyte receiving portion containing a first body fluid fraction that has undergone a separation and a reaction with the first reagent, and a second analyte receiving portion containing a second body fluid fraction that has undergone a separation and a reaction with the second reagent, wherein the camera is configured to capture an image of the first and second analyte receiving portions; and wherein the software contained within the mobile processing device is configured for performing a quantitative analysis of each of the first and second separated and reacted body fluid fractions.

18. The analyte testing apparatus of claim 5 further comprising a light source configured and positioned for illuminating the analyte containing test strip to illuminate the test strip to facilitate the capture of the photographic image of the an analyte containing test strip taken by a digital camera of the mobile telephone.

19. An analyte testing apparatus for providing a quantitative analysis of an analyte of a body fluid placed on an analyte containing test strip, the analyte testing apparatus comprising:

a mobile telephone containing a mobile processing device having a digital camera capable of capturing a photographic image of an analyte containing test strip, the digital camera including a lens, the mobile processing device including software operable by the mobile processing device for processing a photographic image captured by the camera to yield an output comprising a quantitative analysis of an analyte on a test strip, a test wand including a housing, a test strip for receiving an analyte of a body fluid, and a test strip holder for holding the test strip on to the housing, and a positioner for coupling the test wand to the mobile telephone wherein the analyte of the body fluid on the test strip is positioned in the optical path of the lens of the digital camera so that the digital camera is positioned for capturing a digital photographic image of the analyte, so that the image so captured can be processed by the software to perform the quantitative analysis.

20. The analyte testing system of claim 19 further comprising a casing that includes a phone receiving portion configured for detachably coupling the casing to the mobile phone containing mobile processing device.

21. The analyte testing apparatus of claim 19, wherein the test strip positioner positions the test strip in a position out of an undiverted optical path of the lens of the digital camera, and wherein the casing includes an optical path diverter between the lens and the test strip for permitting the camera to capture an image of the analyte containing test strip.

22. The analyte testing apparatus of claim 21 wherein the optical path diverter comprises at least one mirror for reflecting an image of the analyte containing test strip into the lens.

* * * * *